United States Patent
Kunz (10) Patent No.: US 8,432,263 B2
(45) Date of Patent: Apr. 30, 2013

(54) SYSTEM AND METHOD FOR THE COLLECTION, STORAGE, ANALYSIS AND REPORTING OF EVENT INFORMATION

(76) Inventor: Linda H. Kunz, Cedarburg, WI (US)

( * ) Notice: Subject to any disclaimer, the term of this patent is extended or adjusted under 35 U.S.C. 154(b) by 614 days.

(21) Appl. No.: 12/444,466

(22) PCT Filed: Oct. 6, 2006

(86) PCT No.: PCT/IB2006/053675
§ 371 (c)(1),
(2), (4) Date: Apr. 6, 2009

(87) PCT Pub. No.: WO2008/041062
PCT Pub. Date: Apr. 10, 2008

(65) Prior Publication Data
US 2010/0007472 A1    Jan. 14, 2010

(51) Int. Cl.
*H04Q 5/22* (2006.01)
*G05B 19/00* (2006.01)
*G08B 5/22* (2006.01)
*G08B 1/08* (2006.01)
*G08C 19/16* (2006.01)
*G08C 19/12* (2006.01)

(52) U.S. Cl.
USPC ........... 340/10.6; 340/10.5; 340/5.1; 340/5.2; 340/5.6; 340/8.1; 340/539.1; 340/12.1; 340/13.1

(58) Field of Classification Search ............... None
See application file for complete search history.

(56) References Cited

U.S. PATENT DOCUMENTS

| 6,100,806 | A | 8/2000 | Gaukel |
| 6,346,886 | B1 * | 2/2002 | De La Huerga ............ 340/573.1 |
| 6,369,803 | B2 * | 4/2002 | Brisebois et al. ............. 345/173 |
| 6,408,330 | B1 | 6/2002 | DeLaHuerga |
| 6,466,125 | B1 | 10/2002 | Richards et al. |
| 6,779,024 | B2 | 8/2004 | DeLaHuerga |
| 7,088,233 | B2 * | 8/2006 | Menard ...................... 340/539.1 |
| 7,248,933 | B2 * | 7/2007 | Wildman ........................ 700/90 |
| 7,323,991 | B1 * | 1/2008 | Eckert et al. ................ 340/572.1 |
| 7,899,910 | B1 * | 3/2011 | Mosleh et al. ................. 709/227 |

(Continued)

FOREIGN PATENT DOCUMENTS

| JP | 10295652 | 10/1998 |
| JP | 2001 216421 | 10/1999 |

(Continued)

*Primary Examiner* — Daniel Wu
*Assistant Examiner* — Emily C Terrell
(74) *Attorney, Agent, or Firm* — Joseph S. Heino; Patrick M. Bergin (57) ABSTRACT

A system and method includes an RFID tag that is associated with an object or person. The object or person can actuate a call signal to summon a responder, who would be a person fitted with a BODYWARE™ electronic device that is compatible with electromagnetic signals from the RFID tag. As the responder moves into proximity to the RFID tag, initial information is acquired by a BODYWARE™ electronic device from the signals being emitted by the RFID tag. This cues the responder appropriately for the next step of inputting additional event information or data, which information or data is collected, stored, analyzed and reported as is desired or required by the particular system with which the invention is used. Means are also provided to actuate training methodology to maximize the likelihood of acquiring accurate event data, with feedback being provided to the responder for teaching proper data collection methodology.

14 Claims, 6 Drawing Sheets

U.S. PATENT DOCUMENTS

| | | | |
|---|---|---|---|
| 2002/0064766 A1 | 5/2002 | Cozens et al. | |
| 2002/0095401 A1 | 7/2002 | Redmond et al. | |
| 2003/0013438 A1* | 1/2003 | Darby | 455/419 |
| 2003/0023459 A1* | 1/2003 | Shipon | 705/2 |
| 2003/0069002 A1 | 4/2003 | Hunter et al. | |
| 2003/0083903 A1* | 5/2003 | Myers | 705/2 |
| 2003/0173408 A1 | 9/2003 | Mosher, Jr. et al. | |
| 2004/0193449 A1* | 9/2004 | Wildman et al. | 705/2 |
| 2004/0199056 A1* | 10/2004 | Husemann et al. | 600/300 |
| 2005/0062603 A1 | 3/2005 | Fuerst et al. | |
| 2005/0131738 A1 | 6/2005 | Morris | |
| 2005/0151640 A1 | 7/2005 | Hastings | |
| 2005/0190053 A1* | 9/2005 | Dione | 340/500 |
| 2005/0197775 A1 | 9/2005 | Smith | |
| 2005/0216331 A1 | 9/2005 | Ahrens et al. | |
| 2005/0240423 A1 | 10/2005 | Becker et al. | |
| 2005/0240441 A1* | 10/2005 | Suzuki et al. | 705/2 |
| 2005/0250440 A1 | 11/2005 | Zhou et al. | |
| 2005/0283382 A1 | 12/2005 | Donoghue et al. | |
| 2006/0055552 A1 | 3/2006 | Chung et al. | |
| 2006/0080139 A1 | 4/2006 | Mainzer | |
| 2006/0180647 A1 | 8/2006 | Hansen | |
| 2006/0206246 A1 | 9/2006 | Walker | |
| 2006/0219776 A1 | 10/2006 | Finn | |
| 2006/0250271 A1* | 11/2006 | Zimmerman | 340/825.36 |
| 2010/0131296 A1* | 5/2010 | Knutson | 705/3 |

FOREIGN PATENT DOCUMENTS

| | | |
|---|---|---|
| WO | WO 0038156 | 6/2000 |
| WO | WO 0184274 | 11/2001 |
| WO | WO 03013177 | 2/2003 |
| WO | WO 2005019977 | 3/2005 |
| WO | WO 2005076772 | 8/2005 |

\* cited by examiner

FIG. 10

SYSTEM AND METHOD FOR THE COLLECTION, STORAGE, ANALYSIS AND REPORTING OF EVENT INFORMATION

FIELD OF THE INVENTION

The present invention relates generally to the field of computers, peripheral computer devices and software methods that enable user interaction with computers, particularly of the type where data and information is collected and documented via wireless technology. More particularly, it relates to a system and method of data collection, data storage, data analysis, and data reporting in the area of event information of the type that is used to facilitate asset utilization and process optimization in a variety of settings. It also relates to such a system and method that is used in a language and presentation methodology that is adaptive to the variety of individuals with whom and by whom the system and method may be used. Finally, it also relates to a multi-cultural and multi-lingual training system and method to correctively train users of the system and method.

BACKGROUND OF THE INVENTION

In the area of data acquisition, the use of wireless communication devices is well known. Radio frequency identification (RFID) technology, in particular, is well known in the art of wireless communication devices and in the art of electronic identification methods. RFID technology relies on the storage and remote retrieval of data by means of one or more transmission or transponder devices that are frequently called RFID "tags." An RFID tag is a small electronic device that can be attached to or incorporated within a physical item or object for a number of different purposes. RFID tags contain microcircuitry and antennas that enable them to receive and respond to radio frequency queries from an RFID transceiver. Passive tags require no internal power source, whereas active tags typically require a power source.

Current technology known to these inventors includes the use of RFID tags for animal identification. Several attempts have even been made to implement such technology in humans. For example, certain social clubs in Europe have used implantable RFID tags to identify certain "VIP" customers, which tags also allow them to pay for amenities at those facilities. Similarly, a government office of at least one foreign country has implanted RFID tags in various staff members to control access to secure data rooms.

Accordingly, it will be seen that RFID technology is mature and capable of storing the granularity of information that is required for the system and method of the present invention. It is to be understood, however, that wireless communication devices may include other types of communication technologies other than RFID. For example, certain wireless and cellular phone technologies may be combined with a wireless network and include devices such as pagers, cell phones, Blackberry® devices, personal digital assistants (PDA), tablet computers, Bluetooth® headsets, desktop personal computers (PCs), laptop computers, kiosks, slate computers and dumb terminals. Each of these technologies, and its ability to operate in the context of the method and system of the present invention, is proven to be effective wireless technology. These technologies are mature and capable of storing, processing and providing reporting at the level of granularity required in accordance with the present invention. It is to be understood, however, that such other wireless communication devices and other wireless communication methodologies are included within the scope of the present invention. All of such technologies will be collectively referred to in this application as "RFID technology" or simply "RFID."

In the view of these inventors, there is a need, in the field of data collection, to utilize RFID technology in settings where the collector of data is a person who is fitted electronically with means for recognizing signals and data that is being transmitted via RFID technology to such person. In the scope of the present invention, it is also desirable that the person who is collecting data be able to intelligently interact with the RFID source to allow the accurate and systematic collection of data from the RFID source. Within such a setting, it is desirable that multi-cultural and multi-lingual factors be considered when the interaction is between a collector of data who is of one background and the person from who information is being collected is of another background. It is also desirable that the person who is collecting the data be properly trained to maximize the accuracy of collected data and to correct inaccurately collected data, or to correct the data collection methodology of the person who is collecting data. Finally, it is also desirable that the collected data be available for electronic transmission, storage and usage as may be desired or required by the user of the system and method of the present invention.

SUMMARY OF THE INVENTION

Accordingly, it is an object of the present invention to provide a system and method whereby RFID technology is used in settings where the collector of data is a person who is fitted electronically with means for recognizing signals and collecting data that is being transmitted via RFID technology to such person. It is another object of the present invention to provide such a system and method whereby the person who is collecting data is able to intelligently interact with the RFID source, including the ability to cross cultural and lingual barriers, to allow the accurate and systematic collection of data from the RFID source. It is still another object of the present invention to provide such a system and method whereby the person who is collecting the data can be trained to maximize the accuracy of collected data and to correct inaccurately collected data or to correct data collection methodologies that are less than optimal. Finally, it is yet another object of the present invention to provide such a system and method whereby the collected data is available for electronic transmission, re-transmission, storage and usage as may be desired or required by the user of the system and method of the present invention.

The system and method of the present invention has obtained these objects. It provides for one or more RFID tags that are associated with a like number of corresponding objects or persons. Each object or person that is fitted with an RFID tag also has the ability or means to actuate a call mechanism or device for the purpose of summoning a responder, who would be a person, that person being similarly fitted with a BODYWARE™ electronic device that is compatible with electromagnetic signals that are emitted from the RFID tag. BODYWARE™ is a mark of DaRT Chart Systems, LLC. In this fashion, the BODYWARE™ electronic device is first called or alerted to a condition that is sensed by the object or person fitted with the RFID tag by some common server. As the responder physically moves into proximity of the given RFID tag, initial information is acquired wirelessly by the BODYWARE™ electronic device from the signals being emitted by the RFID tag. This provides very initial and preliminary data and information about the object or person fitted with the RFID tag, all with the intention of cueing the responder appropriately for the next step of inputting additional event information or data, which information or data is collected, stored, analyzed and reported as is desired or required by the particular system with which the invention is intended to be used. Means are also provided to actuate training methodology to maximize the likelihood of acquiring accurate event data, with feedback being provided to the responder for teaching proper data collection methodology.

The foregoing and other advantages of the system and method of the present invention will be further apparent from the detailed description that follows.

DETAILED DESCRIPTION

Referring now to the drawings in detail, wherein like numbered elements refer to like elements throughout, FIGS. 1 through 7 illustrate, in schematic form, one preferred embodiment that utilizes the system and method of the present invention. Although the example given here, which example is given solely for the purpose of illustrating enablement of the present invention, is one where the system and method of the present invention is used in a nursing home type setting where information and data is collected and reported for purposes of assisting in the reimbursement of the nursing home by Medicare, it is to be understood that the system and method of the present has much greater applicability. For example, the system and method of the present invention could be applied in industrial settings to monitor and control manufacturing processes, in office settings to monitor and control work flow, and in institutional settings to monitor and control personnel and personnel performance, to name a few. All of such applications are contemplated as being improved through use of the system and method of the present invention with suitable adaptation being made to the particular requirements of each application.

As applied to the specific application disclosed herein, it is to be understood that the goal is to collect and report Minimum Data Set (MDS) data that is used for nursing home resident assessment and care screening. This form is discussed in greater detail in co-pending application, PCT App. No. PCT/US 2004/043177, entitled "MULTI-CULTURAL AND MULTIMEDIA DATA COLLECTION AND DOCUMENTATION COMPUTER SYSTEM, APPARATUS AND METHOD." In general, the form includes data and observation documentation that is essentially mandated by the Medicare program. The MDS form includes a plurality of patient-sensitive considerations, such as Activities of Daily Living (ADL), self-performance difficulty and support needed patterns, patient communication/hearing patterns, mood and behavior patterns, physical functioning and structural problems, special treatments, and so on. Each consideration presents a plurality of possible responses and the user populates each specific consideration with an appropriate response. As each consideration is presented to the user, the user may choose a given response.

Figure 1:
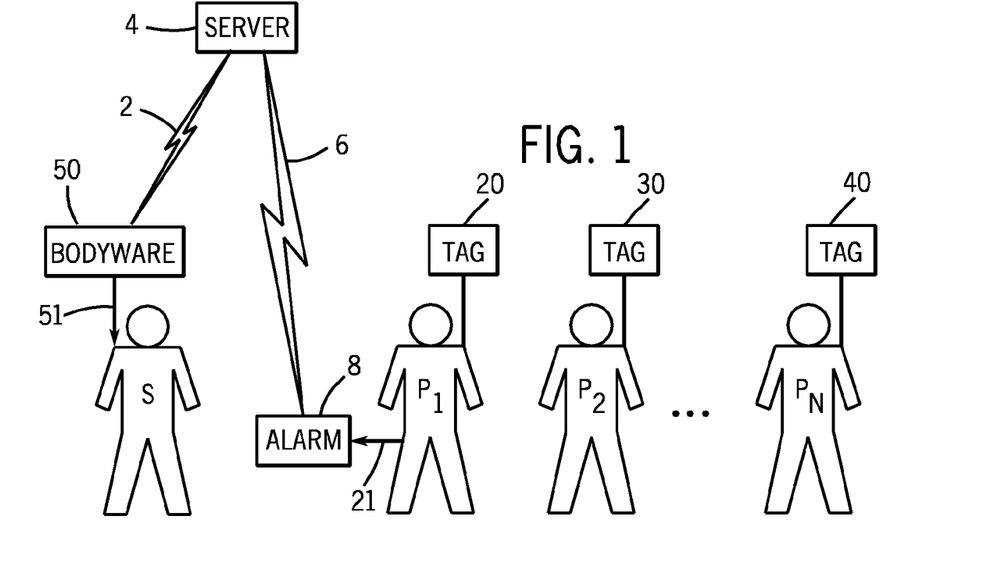
FIG. 1 is a schematic diagram illustrating the outfitting of a number of patients with RFID tags and a member of a facility patient care staff who is equipped with a BODYWARE™ electronic device, the patient alerting the staff member of an event.

Referring now specifically to FIG. 1, which is drawn to the preferred embodiment, it illustrates an indefinite number of patients, identified as $P_1$, $P_2$, and so on, up to $P_N$, which indicate any number of patients within the particular healthcare environment and with which the method and system of the present invention is utilized. Each patient $P_1$, $P_2$, and $P_N$ has an RFID tag 20, 30, 40, respectively, attached to or associated with that particular patient. In the method and system of the present invention, a first patient $P_1$ who requires some sort of intervention by a facility patient care staff member S because of an "event," triggers 21 an alarm 8, which could be a call button or other similar device, which sends a signal 6 to a centralized server 4. The server 4, in turn, sends a signal 2 of its own which is received by a BODYWARE™ electronic device 50 of a particular staff member S, which BODYWARE™ electronic device 50 informs 51 the staff member S of the event. In this fashion, the first patient $P_1$ signals the staff member S that he or she is in need of some sort of assistance.

Figure 2:
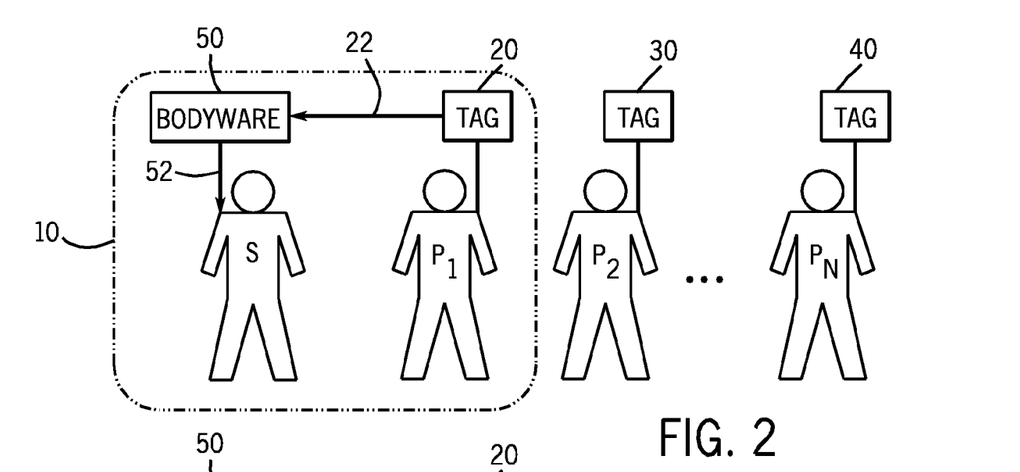
FIG. 2 is a schematic diagram illustrating the interactivity of the patient's RFID tag with the staff member's BODYWARE™ electronic device as the staff member moves into proximity with the patient.

FIG. 2 illustrates that, following the triggering 21 of the alarm 8 by the first patient $P_1$, that the staff member S approaches the first patient $P_1$ and comes within close proximity to the first patient $P_1$. When the staff member S is within a given proximity distance 10 relative to the patient $P_1$, the tag 20 of the first patient $P_1$ transmits, via radio frequency transmission or other suitable transmission means, a signal 22 which provides input to the BODYWARE™ electronic device 50 of the staff member S. At this point, the staff member S is prompted to have access 52 to certain information that is particular to the first patient $P_1$. For example, this information could include, in the setting of a nursing home, who the patient is, what language he or she speaks and what event he or she just experienced. At the same time, the BODYWARE™ electronic device 50 of the staff member S will relay that information to the staff member S such that the staff member S can approach the patient and elicit additional information from that patient using the patient's particular language.

Figure 3:
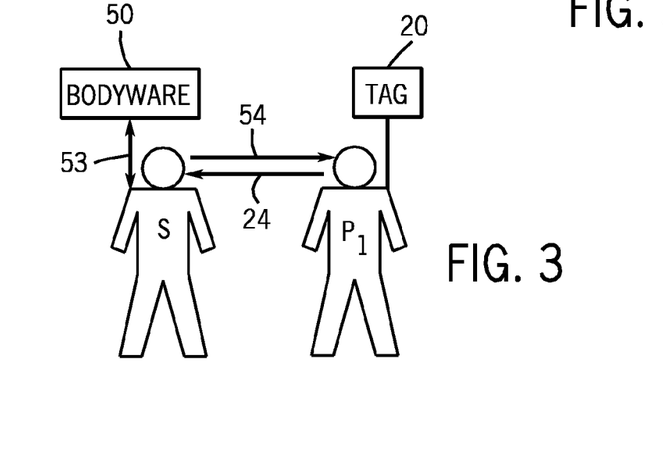
FIG. 3 is a schematic diagram illustrating the interactivity and exchange of information that takes place between the patient and the staff member following the initial collection of RFID tag information by the BODYWARE™ electronic device.
Figure 4:
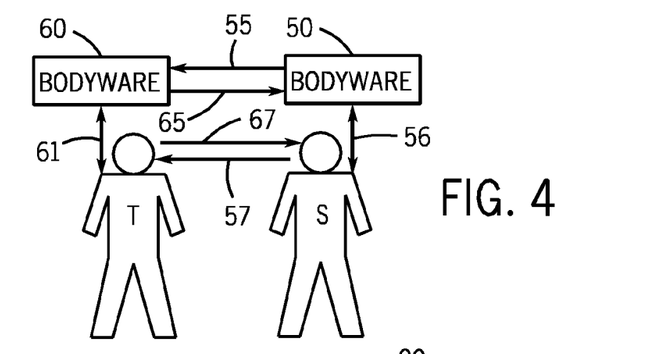
FIG. 4 is a schematic diagram illustrating the interactivity and exchange of information that takes place between the staff member and his or her trainer following the collection of data and information.

As shown in FIG. 3, the staff member S and the first patient P1 will be in proximity to share information that is provided 54 from the first patient P1 to the staff member S and the staff member S will prompt 24 the first patient P1 for certain additional information that is relevant to that patient's care. Additionally, staff member S will be able to obtain information 53 regarding the first patient P1 from the electronic device 50. Staff member S will also be able to add information 53 regarding patient P1 to electronic device 50.

Figure 5:
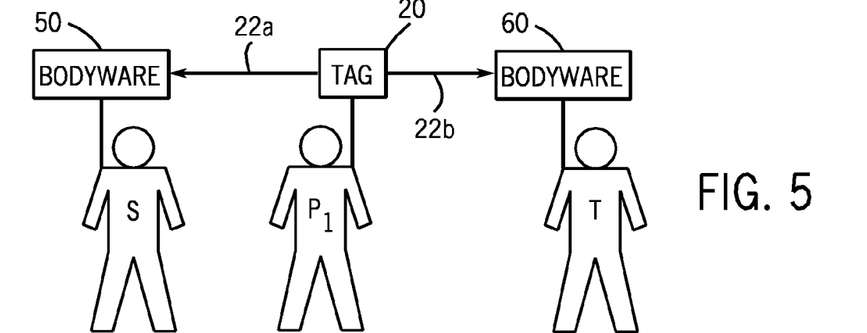
FIG. 5 is a schematic diagram illustrating the alternative interactivity of the patient's RFID tag with the BODYWARE™ electronic device of both the staff member and the trainer.

An additional feature that is incorporated into the system and method of the present invention is the fact that the staff member S will be capable of obtaining immediate training feedback by means of a trainer T who is also equipped with a BODYWARE™ electronic device that is similar to that with which the staff member S is provided. See FIG. 4. This provides means for communication 56, 61 by the staff member S and the trainer T with his or her BODYWARE™ electronic devices 50, 60. This also provides for two-way communication and transmission 65, 55 of information between the respective BODYWARE™ electronic devices 60, 50 worn by the trainer T and by the staff member S, respectively, together with additional verbal dialog 57, 67 from and to each of those persons. In an alternative embodiment, which is shown in FIG. 5, the information and feedback that is provided by the first patient $P_1$ and his or her RFID tag 20 is transmitted 22a to the staff member S and his or her BODYWARE™ electronic device 50 at the same time the trainer T and his or her BODYWARE™ electronic device 60 receives 22b the same information from the first patient $P_1$ tag 20. In this fashion, the trainer T is receiving 22b the same information that the staff member S is receiving 22a and will be provided with information that is common to that patient.

Figure 6:
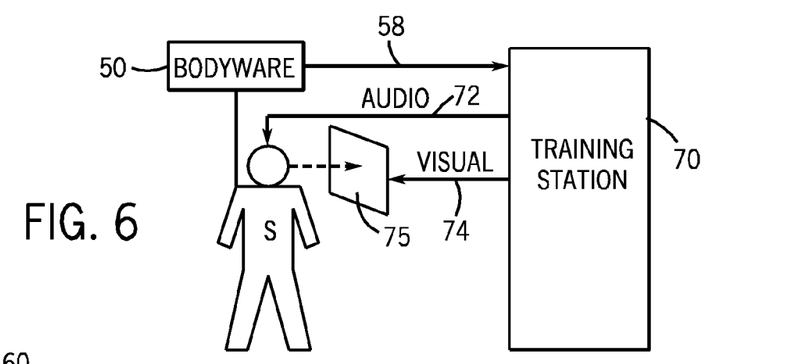
FIG. 6 is a schematic diagram illustrating the alternative interactivity of the staff member's BODYWARE™ electronic device with a training station.
Figure 7:
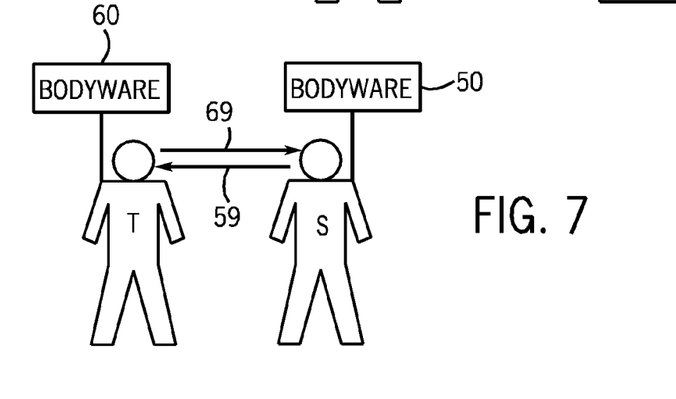
FIG. 7 is a schematic diagram illustrating the alternative training interactivity of the staff member with the trainer.

In an alternative embodiment, which is shown in FIG. 6, the staff member S, together with his or her BODYWARE™ electronic device 50, approaches a training station 70 at which point the BODYWARE™ electronic device 50 will download 58 the responses that were inputted by the staff member S during his or her intervention with the patient $P_1$ and will provide the staff member S with certain audio 72 and/or visual 74 feedback, the visual 74 feedback being provided, for example, by means of a video playback device 75. Alternatively, the trainer T may provide the staff member S with direct verbal feedback 69 as is illustrated in FIG. 7, the staff member S responding appropriately 59 to confirm his or her understanding of corrections that need to be made by the staff member S relative to his or her information collection methodology.

Figure 8A:
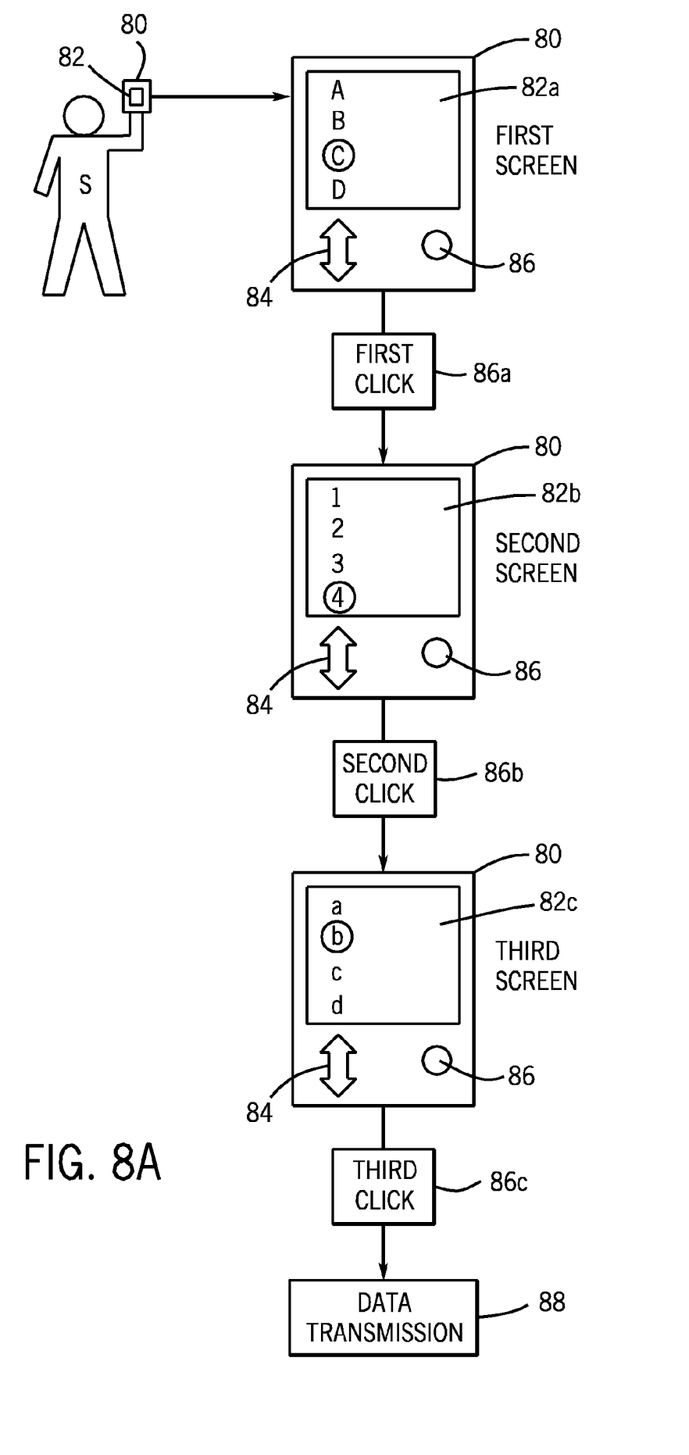
FIGS. 8A and 8B are schematic diagrams illustrating three screen displays on the BODYWARE™ electronic device of the staff member and showing use of the "three click" method for information collection.

Referring now to FIG. 8A, it will be seen that the BODYWARE™ electronic device, now identified 80, that is carried and/or worn by the staff member S includes, in the preferred embodiment, a combination screen display 82 and information transmission means 88. The device 80 would also include a screen display scroll means 84, such as an "up" and "down" scroll key, which would allow the staff member S to scroll up or scroll down a given list of display options. The device 80 would further include an option selection means 86, in the form of a button, which would allow the staff member S to select the most appropriate response to a given query.

As shown in FIG. 8A, a first screen display 82a would be shown to the staff member S upon his or her initial contact with the patient $P_1$. At this point, the screen would display four alternative responses to a first query, the most appropriate of which would be selected by staff member S relative to the particular event that is being responded to. In the preferred embodiment, this would be accomplished by the healthcare provider scrolling down the selection options on the screen display 82a and then "clicking" 86a the select button 86. As shown schematically in FIG. 8A, the staff member S would be presented with four choices—"A," "B," "C" or "D." As shown more specifically in FIG. 8B, the options that would be available would include "toilet," "bed mobility," "transfer" and "eating." In this situation, "transfer" would be the most appropriate response and that is the response that the staff member S would select. Upon this first click, a second screen display 82b of options would be provided to the staff member S.

Figure 8B:
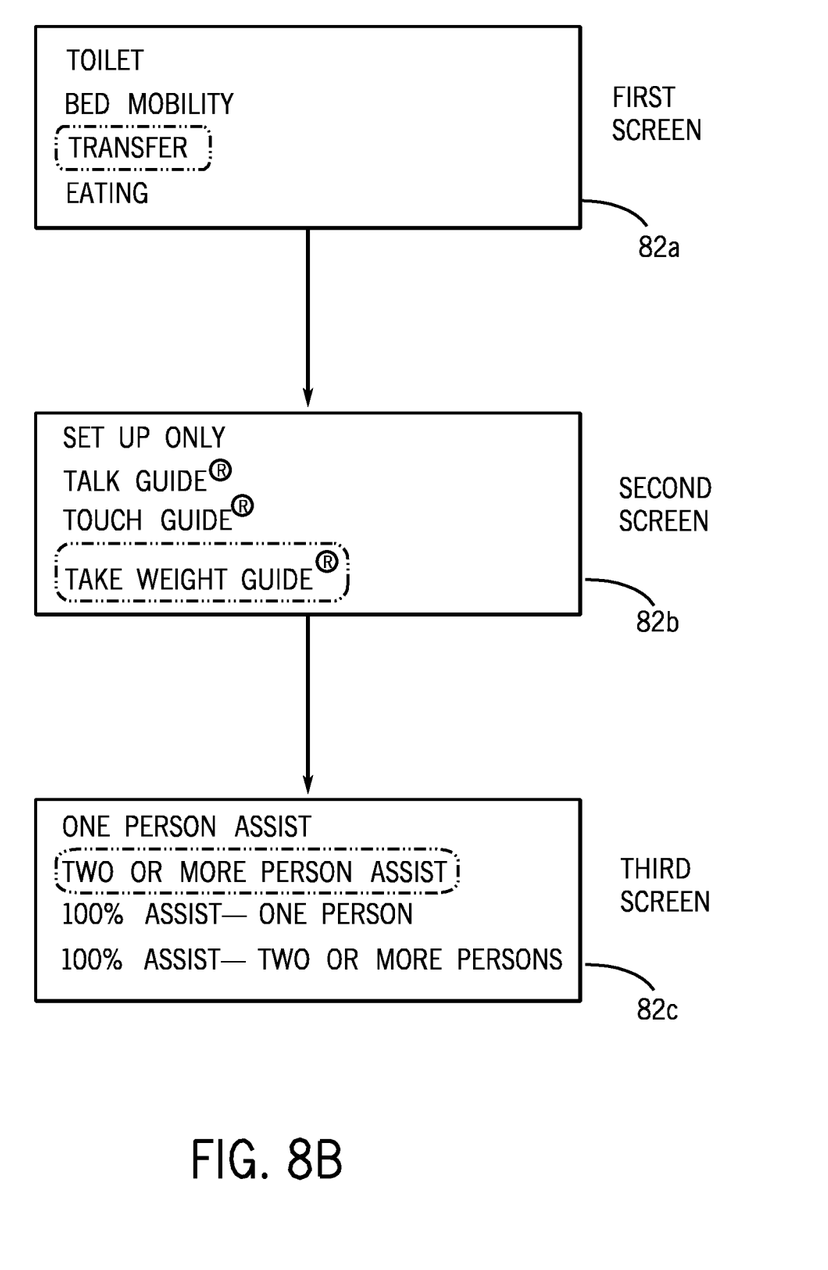

As shown schematically in FIG. 8A, the staff member S would be presented with four choices—"1," "2," "3" and "4." As shown more specifically in FIG. 8B, the available options would be "set up only," "TALK GUIDE®," "TOUCH GUIDE®" and "TAKE WEIGHT GUIDE®." The terms TALK GUIDE®, TOUCH GUIDE® and "TAKE WEIGHT GUIDE® are registered marks of DaRT Chart Systems, LLC. In this situation, "TAKE WEIGHT GUIDE®" would be the most appropriate response and that is the response that the staff member S would select. Upon this second click 86b, a third screen display 82c of options would be provided to the staff member S.

Again, as shown schematically in FIG. 8A, the staff member S would be presented with four more choices—"a," "b," "c" and "d." More specifically, the available options, as shown in FIG. 8B, would be "ONE PERSON ASSIST," "TWO OR MORE PERSON ASSIST," "100% ASSIST—ONE PERSON" and "100% ASSIST—TWO OR MORE PERSONS." In this situation, "TWO OR MORE PERSON ASSIST" would be the most appropriate response and that is the response that the staff member S would select. Upon this third click 86c, the collected data would be transmitted 88 to a centralized server for processing. This "three click" methodology would effectively "disarm" the alarm 8 that was initiated by the patient. It should also be noted that the "three click" method disclosed in this application is intended to enable the staff member S to elicit the maximum amount of information from the patient in the minimum number of steps. In this fashion, time is saved in the overall data collection process. Over time, accuracy of the data collected is ensured due to the staff member's familiarity with this "three click" methodology and the adaptation of the information collection process to the multi-cultural and multi-lingual environment in which it is used.

Figure 9:
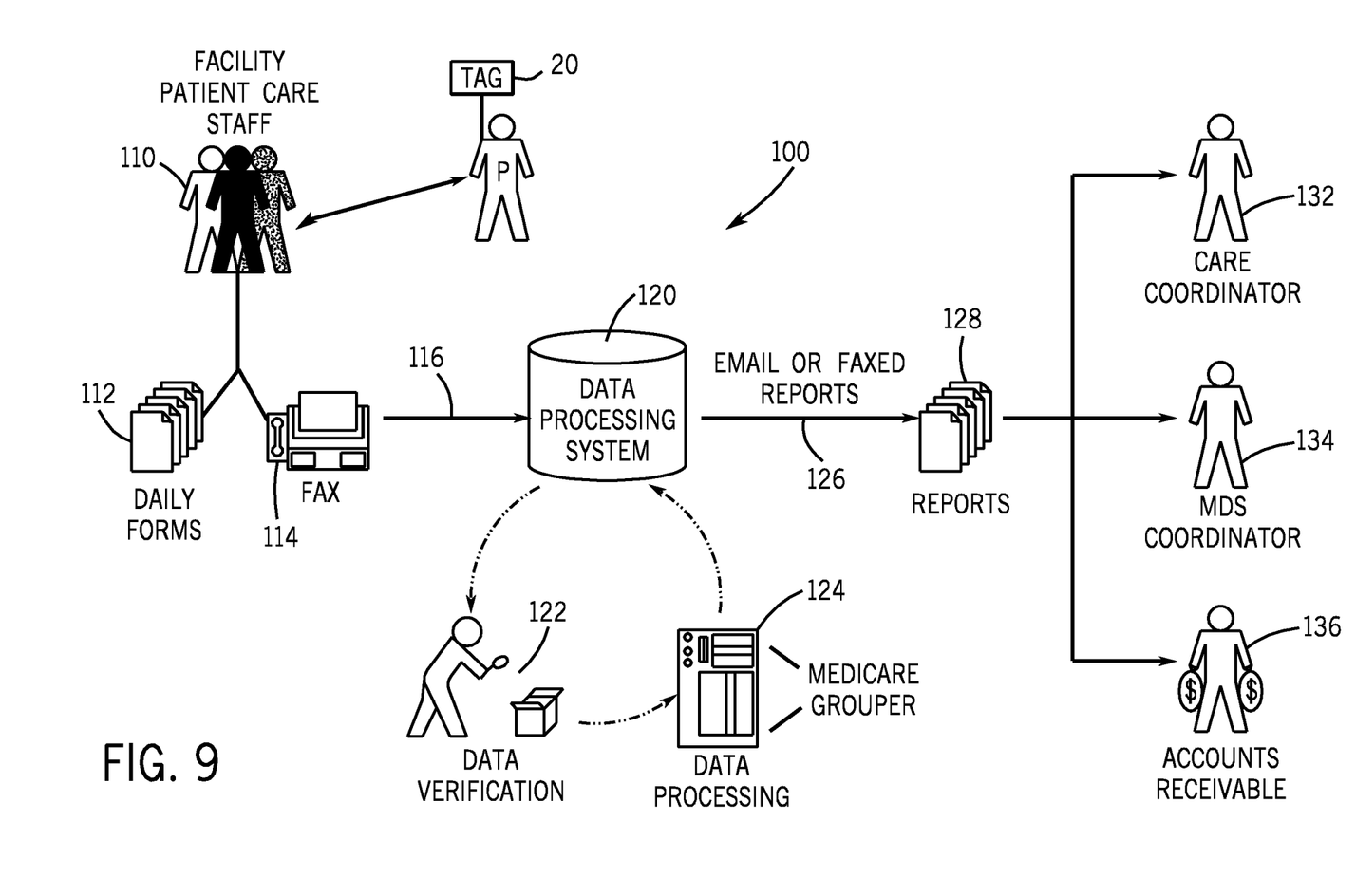
FIG. 9 is a schematic diagram illustrating one preferred embodiment of the system of data collection and reporting in accordance with the present invention.

Referring now to FIG. 9, it will be seen that an overall system workflow schematic diagram for this preferred embodiment is illustrated which shows the interaction between the patient P and his or her tag 20 and the healthcare provider. In general, it will be seen that a system, generally identified 100, within which the system and method of the present invention is incorporated comprises a facility patient care staff 110 that interacts with the patient P, the patient being fitted with a tag 20 as previously described. Once the appropriate information from the patient P is obtained, the facility patient care staff 110 can generate daily forms 112 that can then be faxed 114 via electronic transmission 116 to a data processing system 120. It should be understood that the capturing of appropriate information by the BODYWARE™ electronic device 50, 80 as previously described could also bypass the need to complete daily forms 112 and the need to fax them 114 as shown. Such information transmission could be by electronic and wireless means (not shown) that would directly interface with the data processing system 120. The data processing system 120 of the particular system 100 described herein includes a data verification 122 stage and a data processing 124 stage. The resulting data is then e-mailed or faxed 126 as reports 128 which are then distributed to either a care coordinator 132, an MDS coordinator 134 and/or an accounts receivable 136 department or person. Again, the data contained in the reports 128 could also be transmitted wirelessly to the same recipients using known wireless technology.

Figure 10:
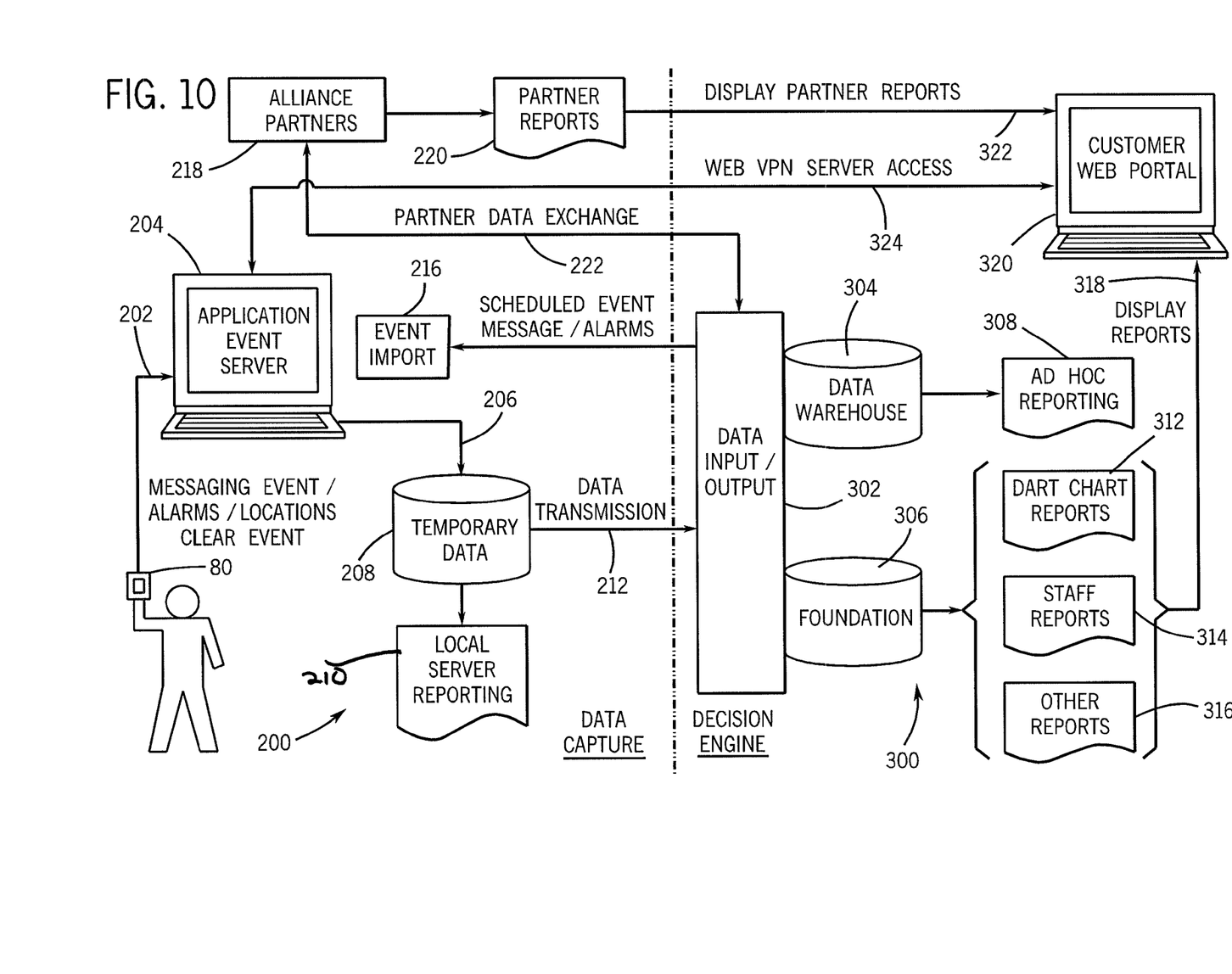
FIG. 10 is a schematic diagram illustrating, in greater detail, the ability of the preferred embodiment to share and utilize data and information that is collected in accordance with the present invention.

As shown in FIG. 10, the generated reports can also be exchanged between various partners with which the system and method of the present invention can be utilized. FIG. 10 is just one example of the method and system of the present invention being used within the preferred embodiment described above. The primary components of the system include a data capture 200 element and a decision engine 300 element. As was previously described, the staff member S, utilizing a BODYWARE™ electronic device 80, is able to message information and events, together with alarms, locations and other relevant information, that is pertinent to a patient within the particular system. The device 80 is also capable of clearing itself once the proper information is reported 202. The information is reported to an application event server 204 which then interacts with a customer web portal 320 by means of a web vpn, or "virtual private network," server access port 324. The application event server 202 is also connected 206 to a temporary data store 208 which provides for local server reporting 210 and data transmission 212 to a primary data input/output engine device 302. The data input/output device 302 includes a bus that connects a data warehouse 304 and a data foundation 306. data input/output 302 also provides schedule event messages and alarms 216. The data warehouse 304 is available for ad hoc reporting 308. Similarly, the data foundation 306 is available to provide various reports 312, 314, 316 which are then displayed 318 on the customer web portal 320. All alliance partners 218 within the system are able to access 222 the data input/output device 302 and are able to generate their own reports 220 which are then displayed 322 on the customer web portal as well.

It is to be understood that the system and method of the present invention, although described in the preferred embodiment as being used within the setting of a nursing home, could be used to collect, store, analyze and report various other event information to facilitate other staff utilizations and other process optimization. This can be done in a variety of multi-cultural and multi-lingual settings that would include multi-cultural and multi-lingual training modules that focus on the correction of trainee errors. The system and method of the present invention could, for example, find wide application in the hospitality industry where participants require the utilization of multi-lingual employees to manage staff and/or interact with guests. The system and method of the present invention could also be adaptable for customer service oriented businesses that service hard assets. For example, the use of the system and method herein would enhance the customer experience by "tagging" the asset at the point of sale or service with customer-specific information. That information could then be used and stored which would then allow for interaction with the customer on subsequent visits and in that customer's particular language. Most importantly, the stored information would be utilized in a way that personalizes it and enhances the customer experience and the responsiveness of the service provider.

In view of the foregoing, it would be apparent that there has been provided a system and method of data collection, data storage, data analysis and data reporting in the area of event information of the type that can be used to facilitate asset utilization and process optimization in a variety of settings; that uses multi-lingual and multi-cultural concepts in both data capture and date presentation methodologies that are adaptive to the wide variety of individuals with whom and by whom the system and method may be used, as well as with assets with which the system and method may be used; and that provides a multi-cultural and multi-lingual training system and method to correctively train users of the system and method. This would utilize training staff and/or training stations that would prompt trainees to view multi-cultural and multi-lingual training modules that focus on the correction of trainee errors and that successfully completes the corrective training and improved understanding of the trainee relative to the events to be captured.

I claim:

1. A system for collecting, storing, analyzing and reporting event information which comprises a central server operable to send and receive electronic signals;

at least one radio frequency identification tag being associable with a person;

an alarm, the alarm being operable by the person, the alarm being operable to initiate an event call signal from the person to the central server and to record a description of the event;

a first electronic device associable with a responder, the first electronic device being in communication with the server and being operable to receive the event call signal, the first electronic device being operable to collect a first set of data or information from the radio frequency identification tag associated with the person when the responder is in proximity to the electronic tag, the first electronic device being operable to receive a radio frequency transmission of information particular to the person comprising the identity of the patient, the language the patient speaks and a description of the event experienced by the person, the first electronic device further comprising a data input means and a data display means, that data input means operable to present a query and a plurality of optional responses to the query on the data display means, to allow a user to select one of the plurality of optional responses to the query, to present additional queries to a user and being operable to transmit the plurality of responses to the query and to the additional queries to the central server; and a second electronic device associable with a trainer, the second electronic device being in communication with the server and being operable to receive and display the same information as is shown on the first electronic device, the second electronic device being operable to record feedback and to transmit the feedback to the first electronic device.

2. The system of claim 1 further comprising means for storing, analyzing and/or reporting the collected second set of data or information.

3. The system of claim 1 wherein the first and second electronic devices that functionally cooperate with the radio frequency identification tag is a device selected from a group consisting of pager,
cellular telephone,
Blackberry® device,
personal digital assistant (PDA),
tablet computer,
Bluetooth® headset,
desktop personal computer (PCs),
laptop computer,
kiosk,
slate computer, or
dumb terminal.

4. The system of claim 3 wherein the first and second electronic devices comprise a combination screen display, information transmission means, screen display scroll means and an option selection means.

5. The system of claim 4 wherein the option selection means comprises a click-type element wherein an option may be selected by clicking the element.

6. The system of claim 5 wherein exactly three clicks of the element are used to collect and transmit all relevant data or information.

7. The system of claim 1 which further comprises means for providing multi-cultural and multi-lingual adaptations for interaction with the object or person.

8. A method for collecting, storing, analyzing and reporting Minimum Data Set information for nursing home resident assessment and care screening which comprises the steps of:
   providing at least one wireless electronic tag that is associated with an object or person;
   permitting initiation of an event call signal from the object or person;
   providing at least one electronic device for use by a staff member, said first electronic device being adapted to cooperatively function with the wireless electronic tag;
   providing at least one electronic device for use by a trainer, said second electronic device being adapted to cooperatively function with the wireless electronic tag;
   providing a server operable to receive event call signals and to communicate electronically with the trainer electronic devices and the staff electronic devices;
   enabling the first electronic devices to collect a first set of data or information comprising the identity of the person, the person's native language and the type of event experienced by the person from the wireless electronic tag associated with a specific object or person when the responder is in proximity to the wireless electronic tag and transmitting the first set of data or information from the wireless electronic tag associated with the specific object or person to the second electronic device;
   displaying the first set of data or information from the wireless electronic tag on the first electronic device;
   displaying the first set of data or information from the wireless electronic tag on the second electronic device;
   enabling the first electronic device to record data input from a user and to transmit the data input from a user to the server, the first electronic device further comprising a data input means, that data input means being operable to present a query and a plurality of optional responses to the query, to allow a user to select one of the plurality of optional responses to the query, to present additional queries to a user and being operable to transmit the plurality of responses to the query and to the additional queries to the central server;
   showing the same queries and plurality of optional responses to the queries on the second electronic device to permit monitoring and training of staff relative to inaccurate or incomplete data or information that is collected on the first electronic device;
   permitting a trainer to record feedback regarding any data entry shown on the second electronic device;
   enabling the second electronic device to send the feedback to the first electronic device;
   enabling the first electronic device to send a signal to the server to turn off the event call signal upon completion of the event call; and
   enabling the server to disarm the event call.

9. The method of claim 8 further comprising the steps of storing, analyzing and reporting the collected second set of data or information.

10. The method of claim 8 wherein the first and second electronic device providing steps include providing an electronic device that functionally cooperates with the wireless electronic tag and is a device selected from a group consisting of
   pager,
   cellular telephone,
   Blackberry® device,
   personal digital assistant (PDA),
   tablet computer,
   Bluetooth® headset,
   desktop personal computer (PCs),
   laptop computer,
   kiosk,
   slate computer, or
   dumb terminal.

11. The method of claim 10 wherein the first and second electronic device providing steps further include providing an electronic device comprising a combination screen display, information transmission means, screen display scroll means and an option selection means.

12. The method of claim 11 wherein the first and second electronic device providing steps further comprise the step of providing an option selection means that comprises a click-type element wherein an option may be selected by clicking the element.

13. The method of claim 12 wherein the first and second electronic device providing steps further include the step of providing an electronic device wherein exactly three clicks of the element are used to collect and transmit all relevant data or information.

14. The method of claim 8 further comprising the step of providing multi-cultural and multi-lingual adaptations for interaction with the object or person.

* * * * *